(12) United States Patent
Lee (10) Patent No.: US 9,849,205 B2
(45) Date of Patent: Dec. 26, 2017

(54) AIR VENTILATING AND STERILIZING APPARATUS MADE OF COPPER

(71) Applicant: NEWON INTERNATIONAL CORP., Clifton, VA (US)

(72) Inventor: Kevin W. Lee, Clifton, VA (US)

(73) Assignee: NEWON INTERNATIONAL CORP., Clifton, VA (US)

(*) Notice: Subject to any disclaimer, the term of this patent is extended or adjusted under 35 U.S.C. 154(b) by 0 days.

(21) Appl. No.: 14/936,639

(22) Filed: Nov. 9, 2015

(65) Prior Publication Data

US 2017/0128607 A1    May 11, 2017

(51) Int. Cl.
*A62B 7/08*    (2006.01)
*A61L 9/00*    (2006.01)

(52) U.S. Cl.
CPC ........... *A61L 9/00* (2013.01); *A61L 2209/134* (2013.01)

(58) Field of Classification Search
CPC .............................. A61L 2209/134; A61L 9/00
USPC ......................................................... 422/122
See application file for complete search history.

(56) References Cited

U.S. PATENT DOCUMENTS

| 7,340,906 | B2 * | 3/2008 | Moffitt | .............. F24F 3/1423 |
| | | | | 62/271 |
| 2004/0194490 | A1 * | 10/2004 | Lee | .............. F24F 3/1423 |
| | | | | 62/271 |
| 2015/0219367 | A1 * | 8/2015 | Kadle | .............. F25B 21/02 |
| | | | | 62/3.2 |

* cited by examiner

*Primary Examiner* — Kevin Joyner
(74) *Attorney, Agent, or Firm* — Novick, Kim & Lee, PLLC; Jae Youn Kim (57) ABSTRACT

Provided is an air ventilating and sterilizing apparatus made of copper plates. The apparatus has a plurality of copper plates to form a plurality air passages for inflowing air, and another plurality of air passages for outflowing air, through which the air flows out and in, and heat is exchanged and air is sterilized while the air flows through the air passages defined by the copper plates each having protruded areas to enlarge the entire surfaces of the plate in contact with the air to maximize the heat exchanging and sterilizing effects of the apparatus.

11 Claims, 9 Drawing Sheets

AIR VENTILATING AND STERILIZING APPARATUS MADE OF COPPER

BACKGROUND OF THE INVENTION

1. Field of the Invention

One or more embodiments of the present invention relate to an air ventilating and sterilizing apparatus made of copper. In particular, the present invention is directed to an air ventilating apparatus for circulating, cleaning and sterilizing air and further heat-exchanging in the air by using a copper plate assembly having multiple thin copper plates with an antimicrobial effect. More particularly, the present invention relates to an apparatus for exchanging incoming air and outgoing air at the same time when ventilating air for residential buildings. The present invention is also focused on the function to preserve the indoor temperature without using additional electric power when the temperature gap between inside and outside temperature occurs, thereby saving energy. In other words, the present apparatus is configured to maintain the indoor temperature without wasting additional energy even in the temperature differences occurring when the warm and cold air is exchanged inside the closed room. Further, the apparatus is configured to change polluted air containing yellow-dust, smog, heavy metal, and micro dust to very fresh air to flow inside the building. It also works as an air exchanger functioning to let the hazy and murky air inside flow out.

2. Description of the Related Art

Conventionally, most homes are being constructed to be airtight for air-conditioning or heating and rely on ventilators or open the windows for letting out the murky air inside the room. These windows are kept closed for heating or air-conditioning, which can cause a lot of problem living in the room full of bad air and decreasing in oxygen through staying inside for long hours.

Accordingly, a variety of solutions to circulate inside air with fresh air from outside have been proposed. However, these solutions have problems resulting a lot of heat loss from radical change in inside and outside temperature and leading to an enormous waste of energy. Further, there is a problem that heat preserving in the room is not well performed when using a conventional air ventilator or circulator that merely ventilates air from inside to outside.

Further, as high-rise residential and office buildings increase, a natural air exchange through windows is getting harder, and degradation of air quality affected by global warming through air pollution and global climate changes have become a controversial issue, as one of global interests. Accordingly, the conventional ventilation system to force the air circulation of inside and outside air has shown the problem that the inside temperature sharply changes. Furthermore, this conventional system allows polluted air containing germs, yellow dust, heavy metal, pollen, smog, micro dust, etc. to come inside without filtering. It shows the forced air circulation by fans lacks the temperature-maintaining and sterilizing capacity of incoming air from outside when the air circulates fast without filtering.

Therefore, an air ventilating and/or sterilizing apparatus is needed that is able to kill bacteria to provide clean air, to prevent inside and outside air from being mixed directly and to perform heat-exchange at the crossing point of inside and outside air, having a heat-exchanging function to save energy.

SUMMARY OF THE INVENTION

Aspects of the invention provide an air ventilating or circulating apparatus made of multiple layers of thin cooper-plates by bending and connecting to each other to make air flow in and out through the space made between the copper-plates and maximize its heat conduction and sterilizing capacity in the process of air-exchange. The apparatus improves the quality of air inside the building and at the same time to save the electric power energy. This apparatus has an outstanding ability to let the clean and fine air in and the hazy murky air out for almost every kind of buildings such as homes, offices, hospitals, schools, department stores, etc.

Therefore, the present air exchanger is designed to be assembled in such a way that both sides of the thin copper-plate facing each other are bent upward and the other sides of the copper-plate facing each other are bent downward to be connected to the next copper-plate. This assembling structure allows the air to cross and flow vertically every floor through side walls with a dual structure of upper walls and lower walls. This also increases the effect of heat conduction and sterilizing capacity by maximizing the staying time of the air-flow in-between through forming the embossing surfaces on the copper-plates.

According to an aspect of the present invention, an air ventilating and sterilizing apparatus is provided. The apparatus includes a copper plate assembly including a plurality of copper plate; a first plurality of air passages disposed in the copper plate assembly, wherein inflowing air passes through the first plurality of air passages; and a second plurality of air passages disposed in the copper plate assembly, wherein outflowing air passes through the second plurality of air passages.

According to an embodiment of the present invention, he air ventilating and sterilizing apparatus includes a first fan configured to direct the inflowing air to pass through the first plurality of air passages from outside to inside a room; and a second fan configured to direct the outflowing air to pass through the second plurality of air passages from inside to outside the room.

According to another embodiment of the present invention, the air ventilating and sterilizing apparatus further includes a case for enclosing the copper plate assembly; and at least one fixture configured to couple the plurality of copper plates.

According to another embodiment of the present invention, the air ventilating and sterilizing apparatus further includes a first vent configured to communicate with the first plurality of air passages, wherein the inflowing air passes through the first vent from outside the room to the first plurality of air passages; and a second vent configured to communicate with the second plurality of air passages, wherein the outflowing air passes through the second vent from inside the room to the second plurality of air passages.

According to another embodiment of the present invention, the air ventilating and sterilizing apparatus further includes a third fan configured to suck air outside the room and discharge the air to the first plurality of air passages; and a fourth fan configured to suck air inside the room and discharge the air to the second plurality of air passages.

According to another embodiment of the present invention, in the air ventilating and sterilizing apparatus, the case includes a front, a back, a right, a left, a top and a bottom side walls, the first fan is disposed on the front side wall and the second fan is disposed on the rear side wall, the first fan and second fan being disposed in line with each other, and the first vent is disposed on the rear side wall and the second vent is disposed on the front side wall, the first vent and second vent being disposed in line with each other.

According to another embodiment of the present invention, in the air ventilating and sterilizing apparatus, the at least one fixture includes a first, a second, a third and a fourth stiffeners disposed and connected to a first, a second, a third and fourth edges of the copper plate assembly, respectively, and the first stiffener is fixed to the front side wall between the first fan and the second vent, the second stiffener is fixed to the right side wall, the third stiffener is fixed to the rear side wall between the second fan and the first vent, and the fourth stiffener is fixed to the left side wall.

According to another embodiment of the present invention, the air ventilating and sterilizing apparatus further includes an inflow air passage defined by the first vent, the first plurality of air passages of the copper plate assembly and the first fan; and an outflow air passage defined by the second vent, the second plurality of air passages of the copper plate assembly and the second fan.

According to another embodiment of the present invention, in the air ventilating and sterilizing apparatus, each of the plurality of copper plates has an upper surface and a lower surface, and further has a first flange and a second flange, both protruding upward from the upper surface, and a third flange and a fourth flange, both protruding downward from the lower surface.

According to another embodiment of the present invention, in the air ventilating and sterilizing apparatus, each of the plurality of the copper plates is connected to each other, being arranged and stacked with each other alternatively on top of another by a 90 degree, thereby creating the copper plate assembly and the first plurality of air passages and the second plurality of air passages.

According to another embodiment of the present invention, in the air ventilating and sterilizing apparatus, each of the first plurality of air passages and each of the second plurality of air passages are disposed alternatively on top of another, thereby one of the first plurality of air passages is disposed between two of the second plurality of air passages or one of the second plurality of air passages is disposed between two of the first plurality of air passages.

According to another embodiment of the present invention, in the air ventilating and sterilizing apparatus, each of the first plurality of air passages is disposed in a same direction, and each of the second plurality of air passages is disposed in another same direction, and the first plurality of air passages and the second plurality of air passages are disposed in different directions.

According to another embodiment of the present invention, in the air ventilating and sterilizing apparatus, each of the plurality of the copper plates is connected to each other by press-fitting the first flange with the third flange, and the second flange with the fourth flange.

According to another embodiment of the present invention, in the air ventilating and sterilizing apparatus, each of the plurality of copper plates has a plurality of protrusions, thereby enlarging the upper and lower surfaces in contact with the inflowing and outflowing air.

According to another embodiment of the present invention, in the air ventilating and sterilizing apparatus, each of the plurality of copper plates has at least one groove configured to reinforce a strength of each copper plate.

According to another embodiment of the present invention, in the air ventilating and sterilizing apparatus, the at least one groove includes a circular groove disposed at a central portion of each copper plate, the central portion being protruded from the upper surface, and at least one elongated groove disposed at a corner of each plate.

According to another embodiment of the present invention, in the air ventilating and sterilizing apparatus, each of the plurality of copper plates has a thickness of 0.1 to 1 mm.

BRIEF DESCRIPTION OF THE DRAWINGS

These and other aspects will become apparent and more readily appreciated from the following description of the embodiments, taken in conjunction with the accompanying drawings of which.

The features and advantages of the present invention will become more apparent from the detailed description set forth below when taken in conjunction with the drawings in which like reference numbers indicate identical or functionally similar elements.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. Terms used herein are for descriptive purposes only and are not intended to limit the scope of the invention. The terms "comprises" and/or "comprising" are used to specify the presence of stated elements, steps, operations, and/or components, but do not preclude the presence or addition of one or more other elements, steps, operations, and/or components. The terms "first", "second, and the like may be used to describe various elements, but do not limit the elements. Such terms are only used to classify one element from another.

These and/or other aspects will become apparent and more readily appreciated from the following description of embodiments of the present invention, taken in conjunction with the accompanying drawing.

Figure 1:
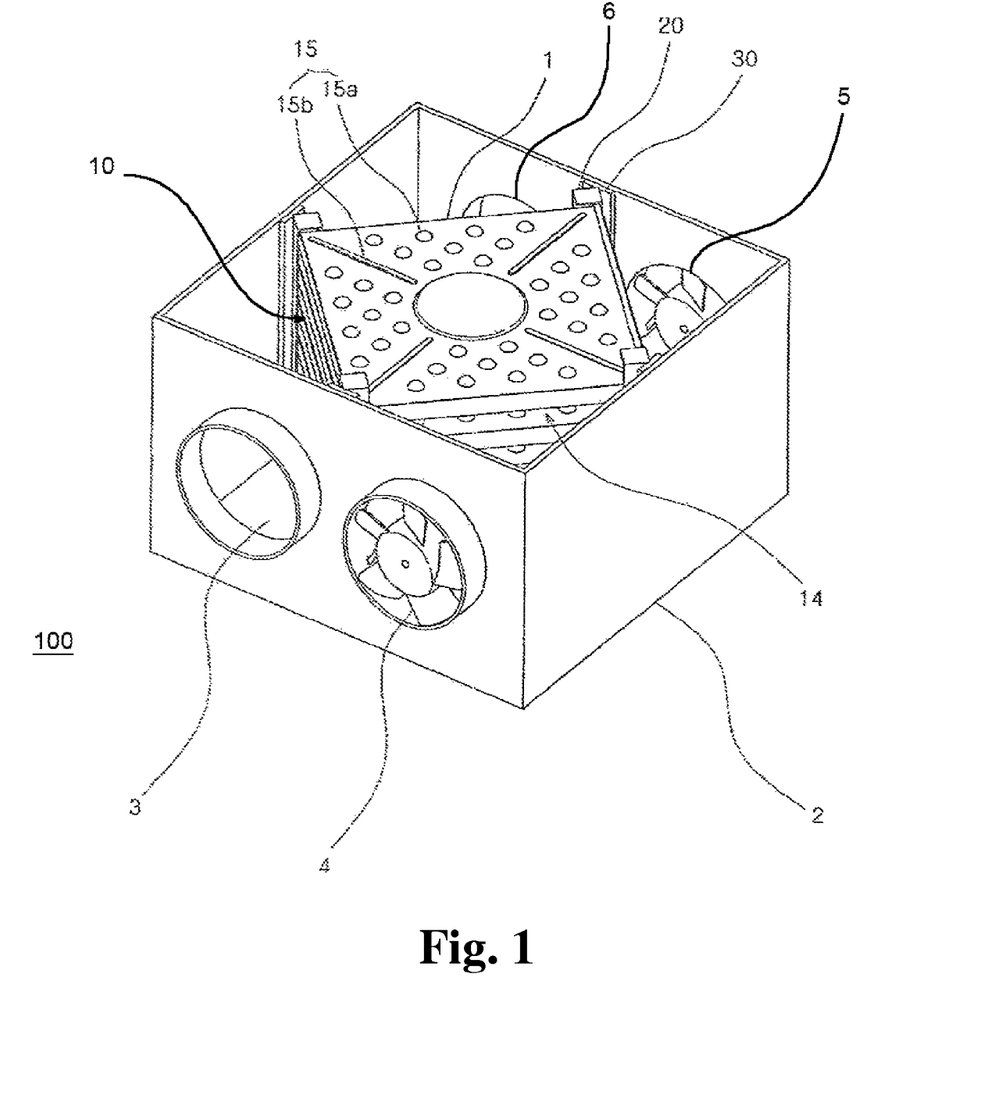
FIG. 1 is a perspective view of one embodiment of an air ventilating apparatus of the present invention.

Referring to FIG. 1 which is a perspective view of one embodiment of an air ventilating apparatus of the present invention, an air ventilating and sterilizing apparatus (100) includes a copper plate assembly (10) including a plurality of copper plate (1), a first plurality of air passages (14) disposed in the copper plate assembly (10), through which inflowing air passes and flows into a room, and a second plurality of air passages (16) disposed in the copper plate assembly (10), through which outflowing air passes and flows outside the room.

The apparatus (100) further includes a first fan (4) configured to direct the inflowing air to pass through the first plurality of air passages (14) from outside to inside a room, and a second fan (5) configured to direct the outflowing air to pass through the second plurality of air passages (16) from inside to outside the room. Further, the apparatus (100) includes a case (2) for enclosing the copper plate assembly (10), and at least one fixture (20) configured to couple the plurality of copper plates.

Further, the apparatus (100) includes a first vent (6) configured to communicate with the first plurality of air passages (14), where the inflowing air passes through the first vent (6) from outside the room to the first plurality of air passages (14), and a second vent (3) configured to communicate with the second plurality of air passages (16), where the outflowing air passes through the second vent (3) from inside the room to the second plurality of air passages (16).

However, in another embodiment of the present invention, the first vent (6) may be replaced with a third fan (not shown in the drawings) configured to suck air outside the room and discharge the air to the first plurality of air passages (14), and the second vent (3) may be replaced with a fourth fan (not shown in the drawings) configured to suck air inside the room and discharge the air to the second plurality of air passages (16).

Further, the case (2) includes a front, a back, a right, a left, a top and a bottom side walls, where the first fan (4) is disposed on the front side wall and the second fan (5) is disposed on the rear side wall, the first fan (4) and second fan (5) being disposed in line with each other, and where the first vent (6) is disposed on the rear side wall and the second vent (3) is disposed on the front side wall, the first vent (6) and second vent (3) being disposed in line with each other.

The fixture can include inner stiffeners (20), i.e., a first, a second, a third and a fourth stiffeners (20), disposed and connected to a first, a second, a third and fourth edges of the copper plate assembly (10), respectively. The inner stiffeners (20) can be attached on each corner of the bent and connected copper plate (1), and a sealing treatment material (30) can be attached on the contacting part of each stiffener (20) with the inside walls of case (2). The sealing treatment material (30) can be various, such as a sponge and the like.

The first stiffener is fixed to the front side wall between the first fan (4) and the second vent (3), the second stiffener is fixed to the right side wall, the third stiffener is fixed to the rear side wall between the second fan (5) and the first vent (6), and the fourth stiffener is fixed to the left side wall. As such, the apparatus (100) forms an inflow air passage defined by the first vent (6), the first plurality of air passages (14) of the copper plate assembly and the first fan (4), and an outflow air passage defined by the second vent (3), the second plurality of air passages (16) of the copper plate assembly and the second fan (5). Air exchanging may be performed through the plurality of air passages (14, 16), and the copper plate assembly (10) can be installed obliquely in an angle of 90 degrees with respect to the front wall of the case (2). For example, the copper plate assembly (10) can be a rectangular shape when seen from the top and can be arranged at an angle of 45 degrees with respect to the front wall of the case (2). As such, there are spaces between the side walls of the case (2) and the copper plate assembly (10) in the case (1). Alternatively, although it is not shown in the drawings, the copper plate assembly (10) can be in the same shape of the case (2), removing such spaces between the walls of the case (2) and the copper plate assembly (10), such that the first and second air passages (14, 16) can be longer.

Figure 2:
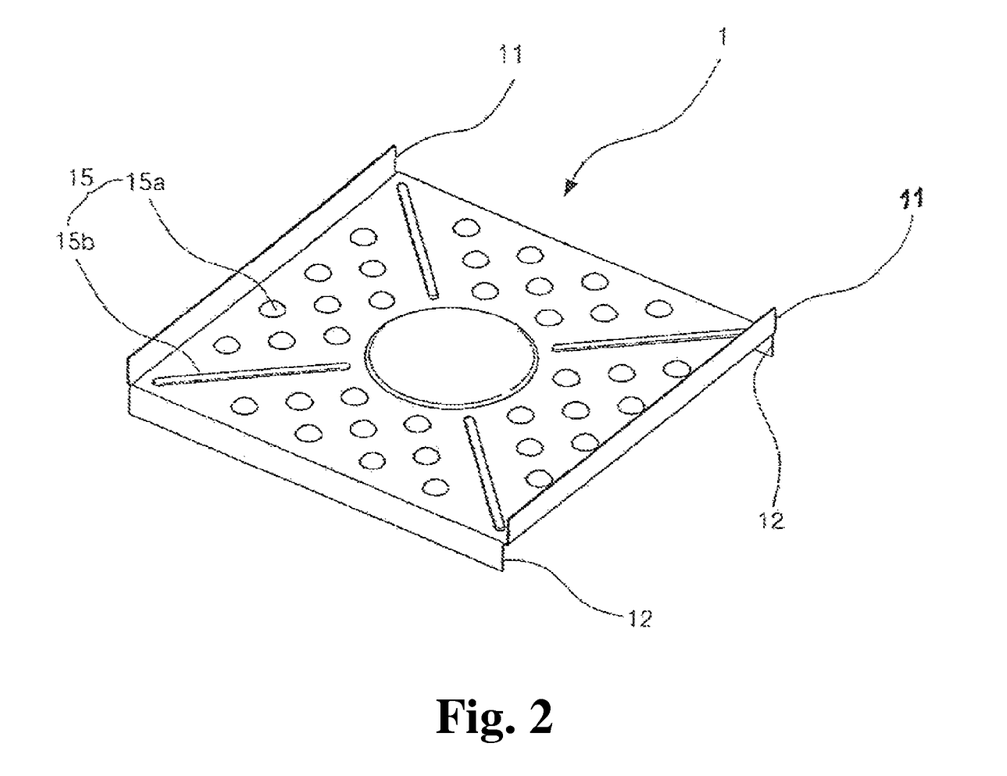
FIG. 2 is a perspective view of a copper plate of the air ventilation apparatus of the present invention.
Figure 3:
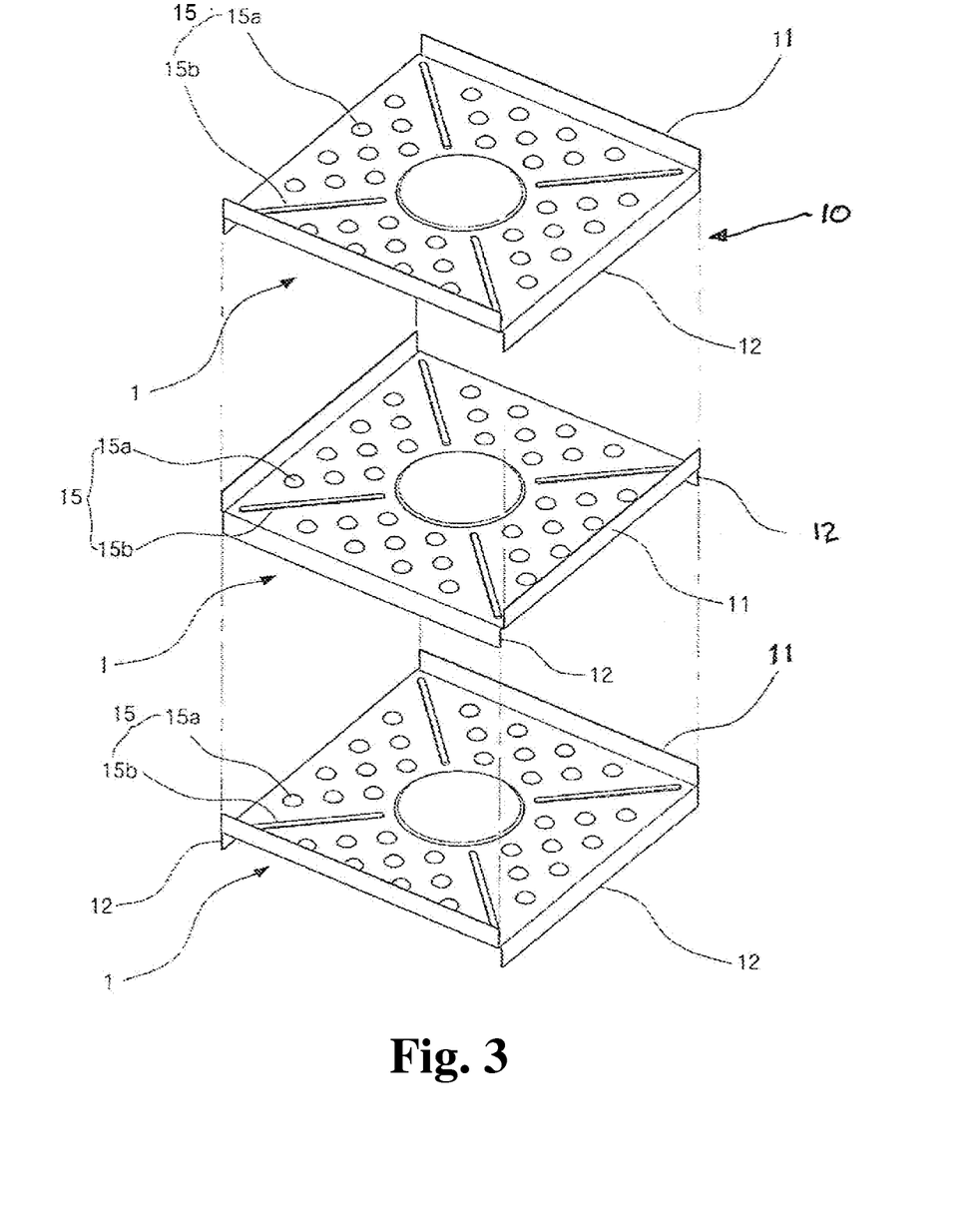
FIG. 3 is a perspective view of a plurality of copper plates showing a method for assembling the plates of the present invention.

With reference to FIGS. 2 and 3, each of the plurality of copper plates (1) has an upper surface and a lower surface, and further has upper flanges (11) on the right and left edges of the plate (1), both of which protruding upward from the upper surface, and lower flanges (12) on the front and rear edges of the plate (1), both protruding downward from the lower surface of the plate (1). To form the copper plate assembly (10), each of the plurality of the copper plates (1) is connected to each other, being arranged and stacked with each other alternatively on top of another by a 90 degree, thereby creating the copper plate assembly (10) and the first plurality of air passages (14) and the second plurality of air passages (16).

Figure 4:
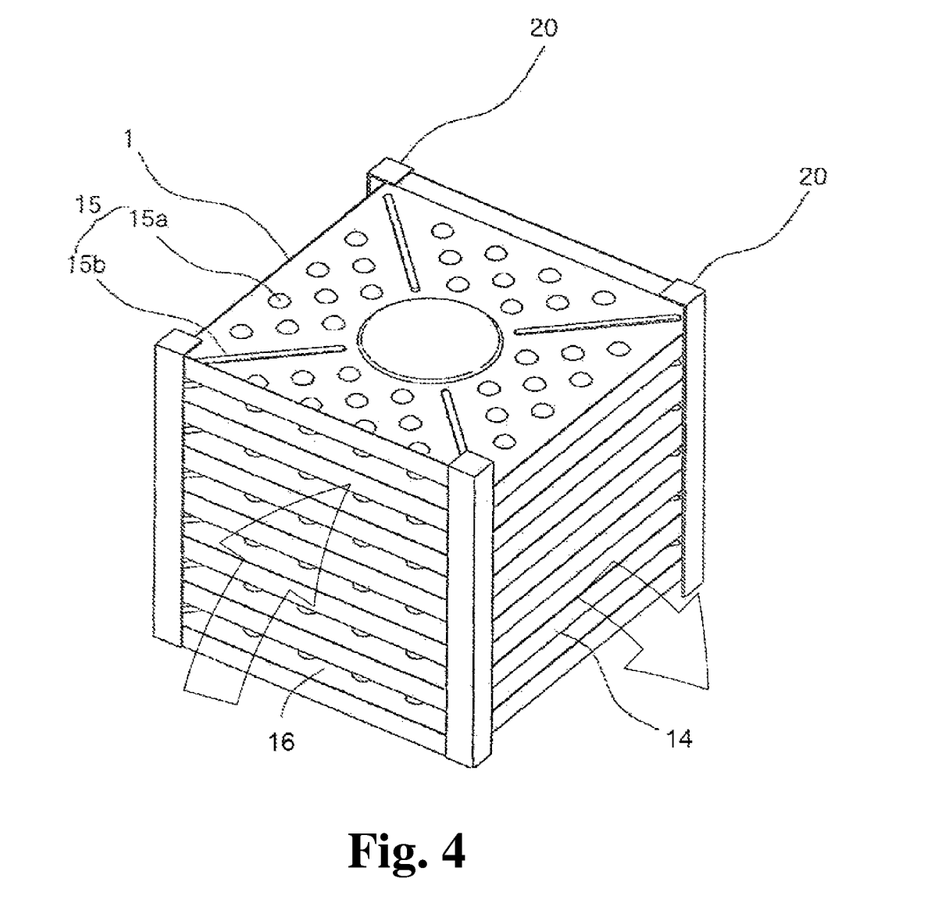
FIG. 4 is a perspective view of a copper plate assembly of the present invention.
Figure 5:
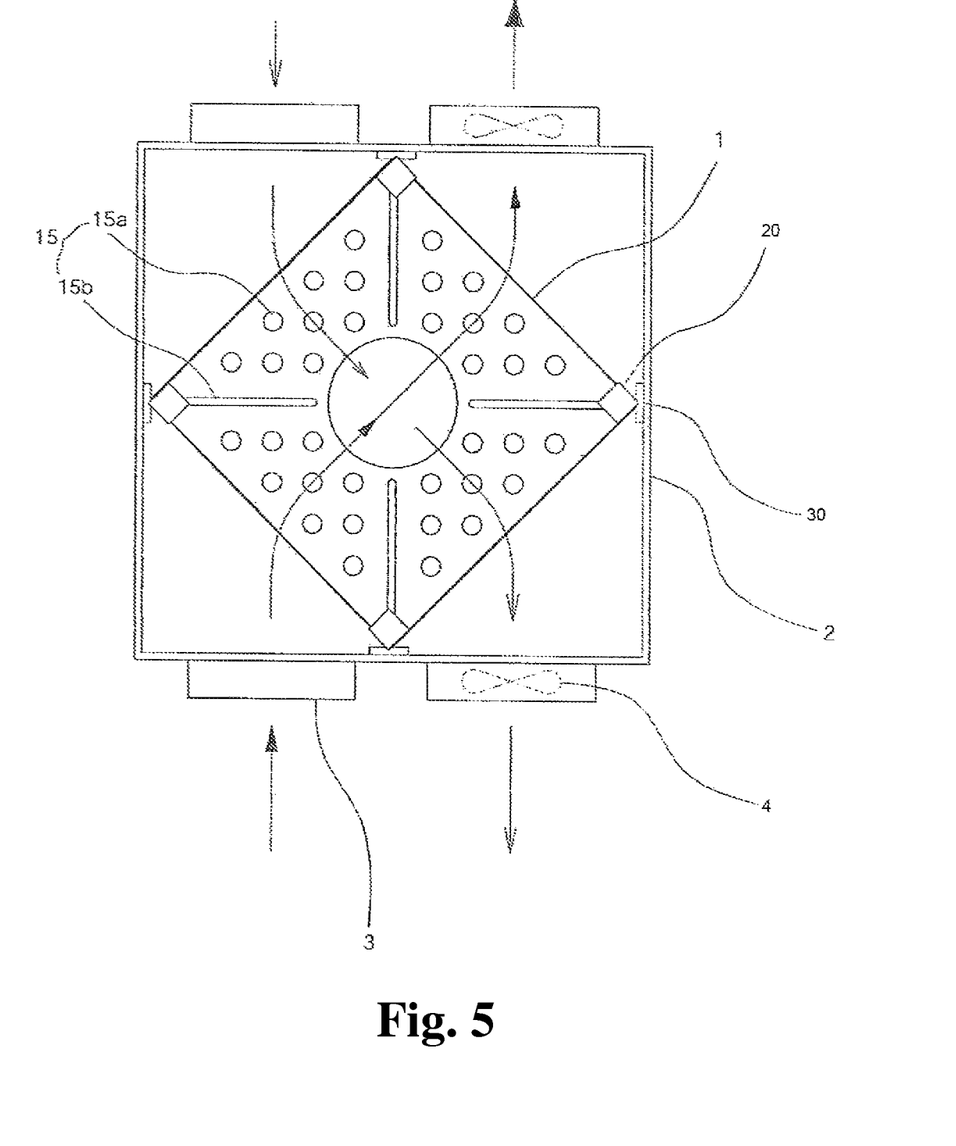
FIG. 5 is a top plan view of the apparatus of the present invention.
Figure 6:
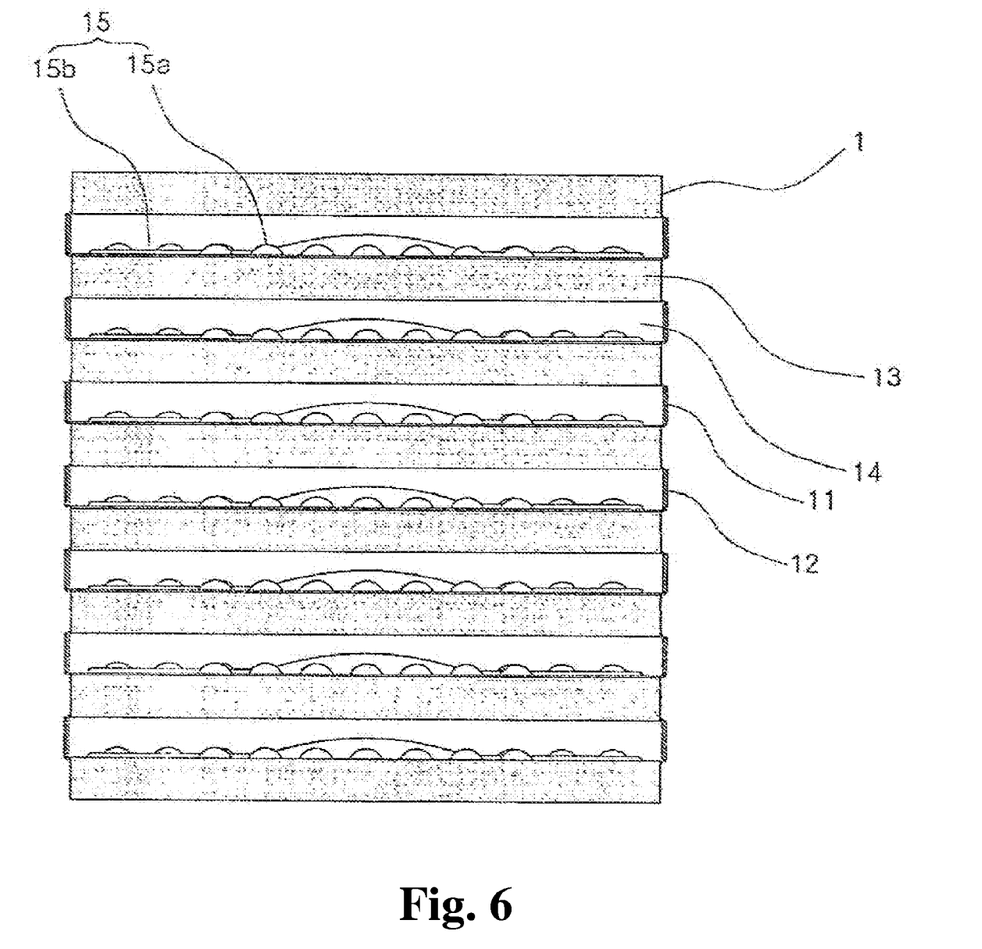
FIG. 6 is a side view of the copper plate assembly of the present invention.

Further, as shown in FIGS. 4 and 5, the copper plate assembly (10) is formed as each of the first plurality of air passages (14) and each of the second plurality of air passages (16) are disposed alternatively on top of another, thereby one of the first plurality of air passages (14) is disposed between two of the second plurality of air passages (16) or one of the second plurality of air passages (16) is disposed between two of the first plurality of air passages (14). The arrows in FIGS. 4 and 5 show the directions of air flows, where the plurality of copper plates (1) are arranged such that the air flows into a room through the first air passages (14) and the air flows outside through the second air passages (16). Also, each of the first plurality of air passages (14) is disposed in a same direction, and each of the second plurality of air passages (16) is disposed in another same direction, and the first plurality of air passages (14) and the second plurality of air passages (16) are disposed in different directions as shown in the figure.

As further shown in FIGS. 2, 3, 6-8, the copper plate assembly (10) can be manufactured in such a way that each of the plurality of the copper plates (1) is connected to each other by press-fitting the upper flanges (11) with the lower flanges (12). Also, the copper plate (1) has a plurality of protrusions (15a), thereby enlarging the upper and lower surfaces in contact with the inflowing and outflowing air. Further, the copper plate (1) has at least one groove configured to reinforce a strength of each copper plate (1). For example, the copper plate (1) can have a circular groove disposed at a central portion thereof, the central portion being protruded from the upper surface. Further, the copper plate (1) can have elongated grooves disposed at every corner thereof. The arrangement, size and shape of the grooves are not limited thereto but can be any ones that can be applicable to the present copper plate (1). The copper plate (1) has a thickness of 0.1 to 1 mm. As an example, the copper plate (1) used in one embodiment of the present invention has a thickness of 0.1 mm.

Figure 9:
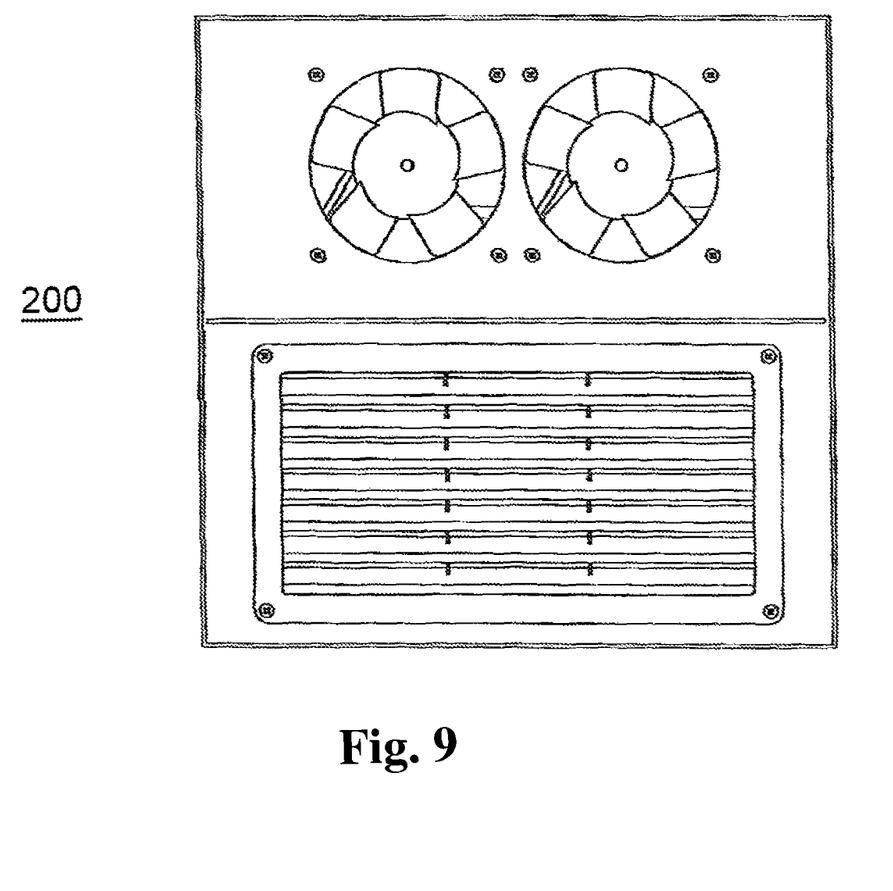
FIG. 9 is another exemplary embodiment of the air ventilating apparatus of the present invention.

Referring FIG. 9 illustrating another embodiment of the present invention, the apparatus (200) may be composed of two units of the apparatus as shown in FIG. 1 with a different arrangement and orientation of the components. For example, the apparatus (200) as shown in FIG. 9 may have two first fans (4) and two second fans (5) on each front and rear sides, and one rectangular vent on each front and rear side. The arrangement and orientation of the components are not limited thereto, but another orientation and arrangement of the components of the present ventilating apparatus may be applicable.

The present air ventilating and sterilizing apparatus can improve the heat conductivity by circulating inside and outside air through the air exchanger built-in the copper plates stepwise bent and connected to each other. In other words, since the first air passages (14) and the second air passages (16) are alternatively arranged in the copper plate assembly (10), where warm air in a room flows and cold air outside flows into the air passages (14, 16) of the copper plate assembly (10), when the warm air and cold air flow through the air passages (14, 16) adjacent to each other, there would be a heat exchange between the two flows of air, such that the air flows in the room would be warmer than the cold air flows into the first air passages (14) during the winter, or vise-versa during the summer.

Figure 7:
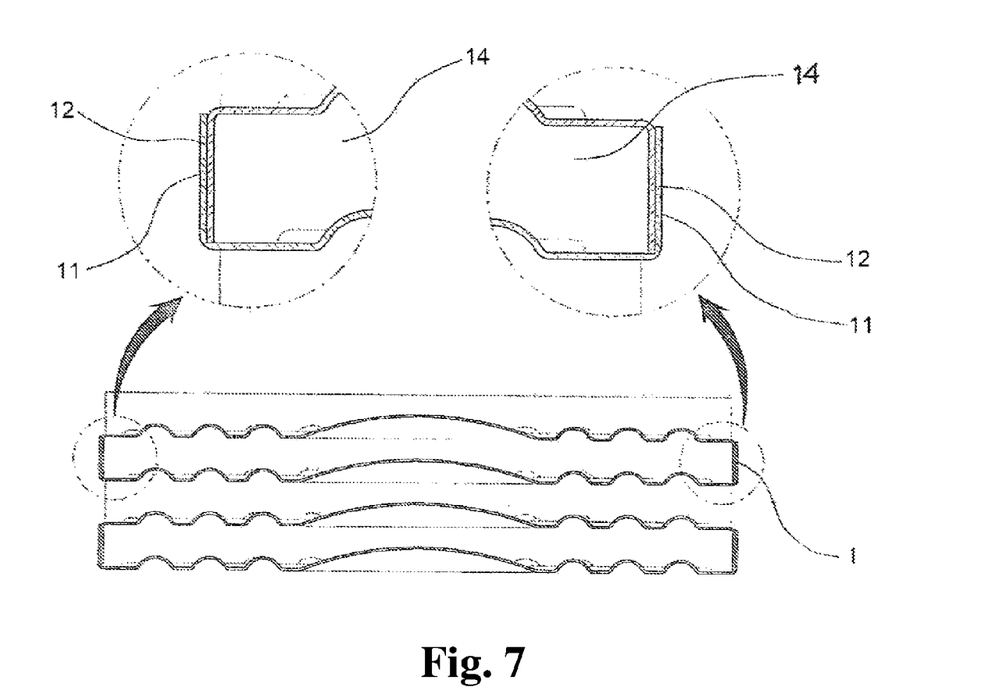
FIG. 7 is an extended view of a portion of the copper plate assembly of the present invention.
Figure 8:
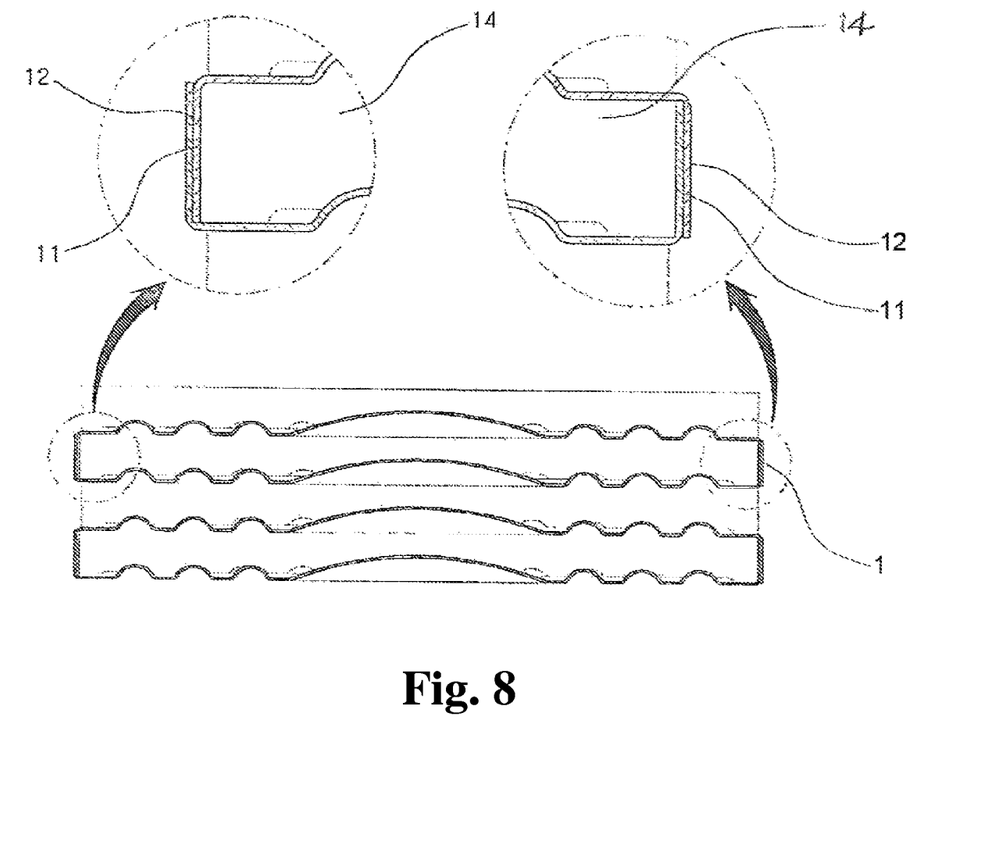
FIG. 8 is another extended view of a portion of another embodiment of the copper plate assembly of the present invention.

Further, the apparatus (100) can serve to increase the effectiveness of the air changer by maximizing the sterilizing capacity of the copper-plates. To achieve this purpose, this invention is designed to have the structure forming the air exchanger made of the multiple copper-plates (1) bent and connected to each other. Each copper-plate (1) forms inside walls (13) including lower walls (flanges (12)) by bending down its front and rear edges and upper walls (flanges (11)) by bending up its left and right edges so that the lower flanges (12) and upper flanges (11) of the copper-plate can be fixed to each other by press-fitting. The plurality of copper plates (1) can be repeatedly connected by the structure of coupling the upper flanges (11) and lower flanges (12) by the press-fitting without welding them each other so that the air-passages (14, 16) can be formed in the directions of front-back and left-right and crossly opened as discussed above. As shown in FIG. 7, the lower flanges (12) can be fitted into the upper flanges (11) or the upper flanges (11) can be fitted into the lower flanges (12) by press-fitting. Alternatively, as shown in FIG. 8, the upper and lower flanges (11, 12) may be fixed together by using an adhesive or welding. When bending the copper plates (1) and connecting the copper plates (1) to each other, as described above, either upper flanges (11) or lower flanges (12) can have a tiny wider width so that one flange can be connected to an inside or outside of another. That is, as illustrated in FIG. 7, the width of the upper flanges (11) can be tiny wider than the width of the lower flange (12) so that the lower flanges (12) get into close to inside the upper flanges (11) to have the dual sealing structure. In the event the space between the upper flanges (11) and the lower flanges (12) are formed evenly, as shown in FIG. 8, they get connected to each other crisscross, which will make the assembly easy and prevents the air from leaking by the dual sealing structure.

The copper-plates (1) also form the embossing area defined by the protrusions (15a) and grooves (15b) to protrude upward or downward in particular. By forming the embossing area in the first and second air passages (14, 16), the copper plates (1) can be touched more widely with air to secure and maximize the heat-exchanging and sterilizing capacity. By forming multiple long and square form of protruding areas in a radial shape from the central area, this apparatus (100) is designed to prevent the copper plates (1) from being twisted and transformed in case of air-exchanging in a high temperature difference between inside and outside the building.

As described above, the copper plates (1) are bent and connected to each other, and therefore, prevent the air from leaking and minimize the heat loss in such a manner to have a dual sealing structure of the upper flanges (11) and lower flanges (12). Further, by continuously bending and connecting the copper-plates (1) by press fitting, manufacturing gets easier, and by circulating inside and outside air, indoor temperature can be maintained sustainable and waste of energy can be minimized. Another effect is that the sterilizing capacity of copper-plates is enhanced by enlarging the contact surfaces of the air passages (14, 16) using the protrusions (15a) and grooves (15b), thereby providing cleaner air in the room inside than outside. As discussed above, another effect of the present invention is that the apparatus (100) can save energy by the heat-exchanging function.

Currently, "the indoor air quality control law for public facilities" is in effect in most of the countries worldwide for public health with the national standard of the permissible level of less than 900 or 1000 PPM.

TABLE 1

Effect of Air Exchanging and Air Cleaning

| Comparison by Places | Index of Air Quality Measurement | Remark |
| --- | --- | --- |
| Natural Environment/ Outdoor Park | 500~650 PPM | Very clean and fresh air |
| Popular Places/ Crowded Subway & Stores | 1,200~2,500 PPM | Yellow Dust, Carbon dioxide, Asbestos, Smoking, Bad Smell, Smog, Atopy, Fine dust, Radon |
| Effect of This Invention | 500~650 PPM | Very clean and fresh air |

TABLE 2

Function of Heat Exchange & Energy Recovery (Saving) Effect

| Season | Outdoor Temperature | Inflow Temperature | Maintain Indoor Temperature | Effect of This Invention |
| --- | --- | --- | --- | --- |
| Summer | 35° C. (95° F.) | 25° C. (77° F.) | 22° C. (71.6° F.) | Cooling → Energy Saving Effect Up to 77% |
| Winter | 0° C. (32° F.) | 18° C. (64.4° F.) | 22° C. (71.6° F.) | Heating → Energy Saving Effect up to 80% |

As shown in Table 2, the present apparatus (100) is configured such that a heat exchange occurs therein while the air passes through the air passages (14, 16) such that the temperature of inflowing air into a room is lower than that of the outdoor temperature in the summer, and higher in the winter. Also, the present apparatus (100) is more effective in air cleaning and sterilizing capacity than a conventional air cleaner.

Recently, laboratory research on the efficacy of Antimicrobial Copper carried out by Professor William Kibble of Southampton University U.K. has been broadcast by the BBC, which is summarized as follows: Stainless steel may look clean, but from zero to 157 deadly bacteria could survive on the surface of this material for 34 days; Antimicrobial Copper is the most effective touch surface material in the fight against pathogenic microbes, killing greater than 99.9% within 4 hours of exposure.

As such, to improve the quality of air from outside the building, this present air ventilating and sterilizing apparatus (100) is designed to have the copper plate assembly (10), each having a thickness as thin as 0.1 mm (0.003937 inch), including ninety one (91) copper-plates due to Copper's excellent ability to kill bacteria.

Each copper plate (1) also has the embossed areas as discussed above so that the air can be stayed in the air passages (14, 16) of the copper plate assembly (10) clean as long as possible and the sterilizing effect can be maximized when the outside air coming in passes through the air passages (14, 16). Due to anions generated by the synergistic effect of Copper and Ion ceramic, clean and fresh air can come inside. For a maximum effect of the invention including energy saving and noise-reduction, special type of cooling fans may be installed.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An air ventilating and sterilizing apparatus comprising:
a copper plate assembly including a plurality of copper plate;
a first plurality of air passages disposed in the copper plate assembly, wherein inflowing air passes through the first plurality of air passages;
a second plurality of air passages disposed in the copper plate assembly, wherein outflowing air passes through the second plurality of air passages;
a first fan configured to direct the inflowing air to pass through the first plurality of air passages from outside to inside a room;
a second fan configured to direct the outflowing air to pass through the second plurality of air passages from inside to outside the room;
a case for enclosing the copper plate assembly; and
at least one fixture configured to couple the plurality of copper plates,
wherein the case includes a front, a back, a right, a left, a top and a bottom side walls, wherein said first fan and said second fan are each mounted to one or more of said side walls of said case.

2. The air ventilating and sterilizing apparatus of claim 1, further comprising:
a first vent configured to communicate with the first plurality of air passages, wherein the inflowing air passes through the first vent from outside the room to the first plurality of air passages; and
a second vent configured to communicate with the second plurality of air passages, wherein the outflowing air passes through the second vent from inside the room to the second plurality of air passages.

3. The air ventilating and sterilizing apparatus of claim 1, further comprising:
a third fan configured to suck air outside the room and discharge the air to the first plurality of air passages; and
a fourth fan configured to suck air inside the room and discharge the air to the second plurality of air passages.

4. The air ventilating and sterilizing apparatus of claim 2, wherein the first fan is disposed on the front side wall and the second fan is disposed on the rear side wall, the first fan and second fan being disposed in line with each other, and
wherein the first vent is disposed on the rear side wall and the second vent is disposed on the front side wall, the first vent and second vent being disposed in line with each other.

5. The air ventilating and sterilizing apparatus of claim 4, wherein the at least one fixture includes a first, a second, a third and a fourth stiffeners disposed and connected to a first, a second, a third and fourth edges of the copper plate assembly, respectively, and
wherein the first stiffener is fixed to the front side wall between the first fan and the second vent, the second stiffener is fixed to the right side wall, the third stiffener is fixed to the rear side wall between the second fan and the first vent, and the fourth stiffener is fixed to the left side wall.

6. The air ventilating and sterilizing apparatus of claim 5, further comprising:
an inflow air passage defined by the first vent, the first plurality of air passages of the copper plate assembly and the first fan; and
an outflow air passage defined by the second vent, the second plurality of air passages of the copper plate assembly and the second fan.

7. An air ventilating and sterilizing apparatus comprising:
a copper plate assembly including a plurality of copper plate;
a first plurality of air passages disposed in the copper plate assembly, wherein inflowing air passes through the first plurality of air passages; and
a second plurality of air passages disposed in the copper plate assembly, wherein outflowing air passes through the second plurality of air passages,
wherein each of the plurality of copper plates has an upper surface and a lower surface, and further has a first flange and a second flange, both protruding upward from the upper surface, and a third flange and a fourth flange, both protruding downward from the lower surface,
wherein each of the plurality of the copper plates is connected to each other, being arranged and stacked with each other alternatively on top of another by a 90 degree, thereby creating the copper plate assembly and the first plurality of air passages and the second plurality of air passages, and
wherein each of the plurality of the copper plates is connected to each other by press-fitting the first flange with the third flange, and the second flange with the fourth flange.

8. The air ventilating and sterilizing apparatus of claim 7, wherein each of the first plurality of air passages and each of the second plurality of air passages are disposed alternatively on top of another, thereby one of the first plurality of air passages is disposed between two of the second plurality of air passages or one of the second plurality of air passages is disposed between two of the first plurality of air passages.

9. The air ventilating and sterilizing apparatus of claim 8, wherein each of the first plurality of air passages is disposed in a same direction, and each of the second plurality of air passages is disposed in another same direction, and wherein the first plurality of air passages and the second plurality of air passages are disposed in different directions.

10. An air ventilating and sterilizing apparatus comprising:
a copper plate assembly including a plurality of copper plate;
a first plurality of air passages disposed in the copper plate assembly, wherein inflowing air passes through the first plurality of air passages; and
a second plurality of air passages disposed in the copper plate assembly, wherein outflowing air passes through the second plurality of air passages,
wherein each of the plurality of copper plates has an upper surface and a lower surface, and further has a first flange and a second flange, both protruding upward from the upper surface, and a third flange and a fourth flange, both protruding downward from the lower surface, wherein each of the plurality of copper plates has a plurality of protrusions, thereby enlarging the upper and lower surfaces in contact with the inflowing and outflowing air, wherein each of the plurality of copper plates has at least one groove configured to reinforce a strength of each copper plate, and wherein the at least one groove includes a circular groove disposed at a central portion of each copper plate, the central portion being protruded from the upper surface, and at least one elongated groove disposed at a corner of each plate.

11. The air ventilating and sterilizing apparatus of claim 10, wherein each of the plurality of copper plates has a thickness of 0.1 to 1 mm.

* * * * *